United States Patent [19]

Murib

[11] 4,208,534

[45] Jun. 17, 1980

[54] PROCESS FOR PREPARING ETHYLENE GLYCOL ESTERS

[75] Inventor: Jawad H. Murib, Cincinnati, Ohio

[73] Assignee: National Distillers and Chemical Corporation, New York, N.Y.

[21] Appl. No.: 972,855

[22] Filed: Dec. 26, 1978

[51] Int. Cl.$^2$ .............................................. C07C 67/05
[52] U.S. Cl. .................................... 560/246; 252/461
[58] Field of Search ................................ 560/245, 246

[56] References Cited

U.S. PATENT DOCUMENTS

| | | | |
|---|---|---|---|
| 3,627,821 | 12/1971 | Sennewald | 560/245 |
| 3,634,496 | 1/1972 | Kominami | 560/245 |
| 3,650,986 | 3/1972 | Sennewald | 560/245 |
| 3,670,014 | 6/1972 | Fernholz | 560/245 |
| 4,016,200 | 4/1977 | Onoda | 560/245 |
| 4,095,037 | 6/1978 | Stapp | 560/246 |

FOREIGN PATENT DOCUMENTS

| | | | |
|---|---|---|---|
| 45-14528 | 5/1970 | Japan . | |
| 46-9446 | 3/1971 | Japan | 560/245 |
| 47-39006 | 12/1972 | Japan | 560/246 |

*Primary Examiner*—Bernard Helfin
*Assistant Examiner*—Michael Shippen
*Attorney, Agent, or Firm*—Kenneth D. Tremain

[57] ABSTRACT

Ethylene glycol esters are obtained from the oxyacylation reaction of ethylene, oxygen and a carboxylic acid in the vapor phase at an elevated temperature and at a controlled pressure in the presence of a catalytically effective amount of a catalyst comprising an oxide of uranium and at least one oxide selected from the group consisting of arsenic, antimony and bismuth oxides.

9 Claims, No Drawings

PROCESS FOR PREPARING ETHYLENE GLYCOL ESTERS

BACKGROUND OF THE INVENTION

This invention relates to a process for preparing ethylene glycol esters by the catalyzed reaction of ethylene, oxygen and a carboxylic acid in the vapor phase.

Ethylene glycol esters are a well known class of organics having widespread use as solvents and plasticizers. Thus, for example, ethylene glycol diacetate is employed as a solvent for cellulose esters and ethers and is often included in resin, lacquer and printing ink formulations. The monoacetate ester of ethylene glycol is used as a solvent for nitrocellulose. Another principal use for ethylene glycol esters is as intermediates in the preparation of corresponding ethylene glycol, which is one of the most industrially important dihydric alcohols.

In view of the considerable commercial significance of the ethylene glycol esters, both as useful products in themselves and as intermediates in chemical synthesis, there is an ongoing need to provide processes for preparing the esters in the most economical manner possible.

Recent years have been an especially active period in the development of processes for obtaining ethylene glycol esters by the one-step catalyzed reaction of ethylene, oxygen and a carboxylic acid. The reaction, commonly referred to as oxyacylation, is usually carried out in the liquid phase at elevated temperature and superatmospheric pressure. Thus for the reaction of ethylene, oxygen and acetic acid to produce ethylene glycol diacetate, the overall chemical reaction can be considered to proceed in accordance with the reaction:

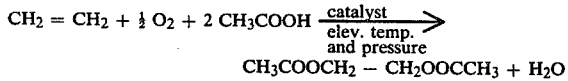

$$CH_2 = CH_2 + \tfrac{1}{2} O_2 + 2\, CH_3COOH \xrightarrow[\text{elev. temp. and pressure}]{\text{catalyst}}$$
$$CH_3COOCH_2 - CH_2OOCCH_3 + H_2O$$

In addition to diester, this reaction will also result in the production of some monoester. Depending in large measure upon the catalyst employed, reactions other than the aforesaid oxyacylation reaction can take place, and to the extent they reduce product yield, complicate recovery and separation techniques and increase raw material and production costs, they are undesirable. The alkylene glycol mono- and diesters are readily hydrolyzed to the glycols and to the carboxylic acid(s) employed in their production employing known and conventional techniques, e.g., hydrolysis by saponification with alkali, or by alcoholysis with acids or acidic ion exchanger.

Numerous proposals for liquid phase oxyacylation catalysts have been made. U.S. Pat. No. 2,519,754 employs as catalyst, a hydrohalide such as hydrobromic acid or an aliphatic halide such as methyl bromide. Snyder's process described in U.S. Pat. No. 2,701,813 employs certain metals or metal compounds such as silver, compounds of metals of the first transition group of the periodic system, particularly their salts, and salts of such heavy metals which are capable of existing in more than one oxidation state such as the acetates, stearates and naphthenates of cobalt, manganese, copper and the like. U.S. Pat. No. 3,479,395 to Huguet describes a process employing tellurium dioxide solubilized with a halide salt. Lutz, in U.S. Pat. No. 3,542,857 employs a cerium (III) or cerium (IV) salt which is soluble in the carboxylic acid component of the oxyacylation reaction medium. U.S. Pat. Nos. 3,668,239 and 3,789,065 to Kollar, and U.S. Pat. No. 3,907,874 to Harvey et al. each employ a source of metal cation such as that of tellurium and a source of bromine. U.S. Pat. Nos. 3,689,535 and 3,985,795 to Kollar and U.S. Pat. No. 3,872,164 to Schmidt each describe a process for preparing ethylene glycol esters by contacting ethylene, bromine or chlorine, or a compound of bromine or chlorine, and oxygen in the presence of a carboxylic acid and a variable metal cation such as antimony cation. Similarly, the Valbert (U.S. Pat. No. 3,715,388) and Hoch (U.S. Pat. No. 3,715,389) catalysts include bromine or a bromine compound and a source of metal cation such as arsenic or antimony cation. U.S. Pat. No. 3,770,813 to Kollar describes the use of a catalyst containing iodine or iodide anion and a heavy metal cation of atomic number 21–30 and 48. U.S. Pat. No. 3,778,468 employs a catalyst containing selenium cation and chlorine, bromine or a compound thereof. Gaenzler et al. U.S. Pat. No. 3,916,011 describes an oxyacylation catalyst which is a complex formed between a compound of titanium and a compound of lithium, beryllium, magnesium, calcium, boron, aluminum, silicon or phosphorus, or a complex formed between compounds of at least two of the elements boron, aluminum, silicon and phosphorus. The oxyacylation catalyst of Gaenzler et al. U.S. Pat. No. 3,981,908 contains a compound of boron, aluminum, silicon, phosphorus or a combination thereof, and a compound of iron, copper or a combination thereof. The Schmerling (U.S. Pat. No. 4,009,203) catalyst is the reaction product of a tin halide and a carboxylic acid.

Each of the aforesaid oxyacylation catalysts is subject to one or more disadvantages, either in regard to the complexity of the apparatus required to carry out the process and/or in regard to the degree of selectivity of the reaction of ethylene, oxygen and carboxylic acid for ethylene glycol ester. In the case of the known catalysts which are intended for use in the liquid phase, the added complexity of operating under liquid phase conditions is a decided drawback. It is recognized that liquid phase systems containing a halogen, oxygen and a carboxylic acid are extremely corrosive and require expensive corrosion-resistant equipment and intensive equipment maintenance.

SUMMARY OF THE INVENTION

The oxyacylation catalysts employed in the process of making ethylene glycol esters according to this invention overcome in large measure the disadvantages associated with the catalysts of the prior art. Since the catalysts herein can be employed in a vapor phase reaction system and eliminate the presence of halogen and halide, there is provided a simpler, more economical and less maintenance-intensive industrial process for efficiently manufacturing a class of organic chemicals of prime economic importance. Moreover, use of the vapor phase facilitates the separation of glycol ester product from the catalyst.

Broadly stated, the process for obtaining ethylene glycol esters according to this invention, comprises reacting ethylene, oxygen and a carboxylic acid in the vapor phase at an elevated temperature and at a controlled pressure in the presence of a catalytically effective amount of a catalyst consisting essentially of an oxide of uranium and at least one oxide selected from the group consisting of arsenic, antimony and bismuth oxides.

In addition to the main product of this process, ethylene glycol ester, minor amounts of other compounds may be obtained, for example, ketone, carbon dioxide and other by-products.

DESCRIPTION OF THE PREFERRED EMBODIMENTS

The ethylene used herein may contain impurities of the type and in the amounts normally present in the commercial grades of this reactant.

The carboxylic acids contemplated herein supply the acyl moiety to the glycol ester and are advantageously selected from the aliphatic monocarboxylic acids containing about 2 to 8 carbon atoms, preferably 2 to 6, and include acetic, propionic, butyric and the like. Aliphatic carboxylic acids having two or more —COOH groups may also be employed.

Of the aforesaid carboxylic acids, the lower aliphatic monocarboxylic acids are preferred and of these, acetic acid is most preferred. It is within the scope of this invention to employ a mixture of different carboxylic acids; however, there will ordinarily be little interest or advantage in doing so since the use of a mixture of acids will only result in a mixture of ethylene glycol esters. The carboxylic acids are usually suitable for use in their concentrated, commercial form. It is preferred that the acids contain no more than about 25 weight percent water and acids having less than about 5 weight percent water are especially preferred. Thus, for example, commercial glacial acetic acid which contains less than 2 weight percent water is well suited for use in the oxyacylation reaction of this invention. Use of large amounts of water admixed with acetic acid results in hydrolysis of the glycol acetate in the reactor which could complicate the separation procedure.

The catalyst herein comprises an oxide of uranium and an oxide of at least one member of the group consisting of arsenic, antimony and bismuth. The aforestated oxides can exist in any of their oxidation states and specifically include uranium dioxide, uranyl uranate, uranium trioxide, the trioxides, tetroxides and pentoxides of arsenic, antimony and bismuth, and mixtures of these oxides. The atomic ratio of uranium to antimony, bismuth and/or arsenic can vary over wide limits and advantageously is within the ratio of about 50:1 to about 1:99. A ratio of 10:1 to 1:10 is preferred. U.S. Pat. No. 3,198,750 discloses a suitable catalyst containing mixed antimony oxide and uranium oxide and a method for preparing the catalyst, said patent being hereby incorporated by reference.

While it is not necessary to provide the catalyst of this invention with a support, it is generally advantageous to deposit the catalysts upon a carrier such as any of the known and conventional catalyst carrier materials since catalytic efficiency will thereby be significantly improved. Thus, the catalysts herein can advantageously be supported upon silica, alumina, zirconia, silica-alumina, silicon carbide, alundum and inorganic silicate in an amount, by weight of metal of the supported catalyst, of about 1 percent to about 90 percent preferably about 10 to 50 percent, catalyst by weight of support material. A preferred catalyst contains about 5% to 30% antimony, bismuth or arsenic, preferably antimony, and 1% to 20% uranium, by weight of the supported catalyst.

Preparation of the supported catalysts follows well-established procedures. A preferred method comprises impregnating the support with an aqueous solution of water soluble compounds of uranium and arsenic, antimony and/or bismuth, followed by drying, e.g., heating at about 100° to 120° C., and calcining in the presence of oxygen at about 350° C. to 900° C., e.g. calcining in air at 450° C. for 12 hours, and at 850° C. for an additional 12 hours. Examples of suitable water soluble metal compounds which can be used in the preparation of the supported catalysts include uranyl nitrate, uranyl chloride, uranyl sulfate, uranyl tetrachloride, arsenic acid, antimony pentachloride and bismuth nitrate. The catalyst bed can be a fixed bed employing a large particulate or pelleted catalyst or, in the alternative, a fluidized bed of catalyst can be utilized. Non-supported catalysts may be prepared by precipitation of the soluble salt or salts from solution by, e.g., neutralization with aqueous ammonia solution, filtration, washing, drying and calcining.

Promoters, such as oxides of molybdenum, thallium, copper and silver may be employed to improve the selectivity and reaction rate. The amount of promoter, by weight of metal on the supported catalyst, is generally within the range of about 0.1–10% preferably 0.5–3.5%.

In general, any apparatus of the type suitable for carrying out reactions in the vapor phase can be used in carrying out the oxyacylation reaction of this invention. The reactor can be brought to the reaction temperature before or after the introduction of the reaction feed mixture. However, in a large-scale operation, it is preferred to carry out the process in a continuous manner and in such a system, the recirculation of unreacted reactants is contemplated.

The concentrations of ethylene, carboxylic acid and oxygen used in the oxyacylation reaction can vary widely. The effective minimum concentration of catalyst will depend upon temperature, residence time and the particular composition of the catalyst employed. The mole ratios of oxygen to olefin to carboxylic acid fed to the reaction zone is not critical but it should be adjusted so that the mixture used is not in the explosive region. The stoichiometric ratio of ethylene:carboxylic acid:oxygen is 2:4:1 and the relative proportions may vary widely. In general, the ethylene may be used in large excess to improve the selectivity to the ester. Broadly stated, in volume percent, based on the total content of ethylene, carboxylic acid and oxygen, the oxygen is about 1%–50%, the carboxylic acid is about 1%–77% and the alpha-olefin is about 1%–98%. A preferred range is about 1% to 20% oxygen, 2% to 35% carboxylic acid and 45% to 97% alpha-olefin. The feed may also be diluted with nitrogen or other inert gas to maintain the mixture outside the explosive limits.

The temperatures employed in the reaction zone are sufficient to maintain the reactants in the vapor state. In the case of ethylene and glacial acetic acid, the temperature range is between about 150° C. and 400° C. and preferable is within the range of from about 250° C. to about 310° C.

An important feature of the invention is the pressure in the oxyacylation zone. In my copending applications filed concurrently herewith it is disclosed and claimed that the reaction processes are dependent mainly upon the olefin employed and the pressure in the reaction zone. Thus, for example, in the application entitled "Process for Preparing Gamma-Lactones" when olefins are reacted at low pressure, up to about 40 psig, gamma-lactones are formed, such as gamma-butyrolactone from ethylene. At high pressures, as in the application entitled "Process for Preparing Esters", oxyacylation of higher olefins, such as propylene produces alkyl acetate as a major product and oxyacylation of ethylene yields ethylene glycol esters as disclosed herein. Oxyacylation of aromatics over a wide range of pressures produces esters, such as benzyl acetate from toluene as described in the application entitled "Process for Preparing Aromatic Esters." In the instant process, it is important to employ a pressure in the oxyacylation zone of the above about 40 psig, preferably above about 60 psig. Pressures higher than about 1000 psig or higher, may be employed, but will normally not be employed due to equipment limitation and increased cost. A preferred range is about 60 to 200 psig, with a highly preferred range being about 85 to 110 psig.

The reaction time will depend largely upon the concentration of reactants and, therefore, may suitably vary over a wide range. Flow rates are preferably adjusted so that the contact time is in the range of about 0.1 to about 60 seconds, and preferably between 1 and 5 seconds.

The following expressions are defined as follows and will be used throughout the disclosure.

The term "% Conversions" means $$\frac{\text{millimoles (MM) in} - \text{MM out}}{\text{MM in}} \times 100$$

of the specified reactant.

The term "Selectivity Component" means $$\frac{\text{MM component}}{\text{MM specified material component}} \times 101$$

The term "Catalyst Utility" means grams component produced/liter catalyst/hour (g/l.cat/hr).

The following examples are illustrative of the invention.

EXAMPLE 1

Preparation of Catalyst

Extruded silica gel, 429.5 grams (g.) (⅛" diameter × ¼" long, 200 m²/g surface area) was placed in a 2-liter beaker and treated with an aqueous solution containing 284.8 g. SbCl$_5$, 90.6 g. UO$_2$(NO$_3$)$_2$.6H$_2$O and 210 g. concentrated HCl. While mixing, the mixture was heated to dryness on a hot plate. The resulting impregnated extrudates were calcined in air at 450° C. for 12 hours followed by calcining in air at 850° for an additional 12 hours.

EXAMPLE 2

Oxyacylation of Ethylene with Acetic Acid and Oxygen at 110 psig and 290° C.

15.1 g. of the catalyst prepared in EXAMPLE 1, was packed in a stainless steel reactor (2.5 cm × 12 cm) provided with a thermocouple imbedded in the catalyst bed. The catalyst was heated at 290° C. A gaseous mixture consisting, by volume, of 72.4% ethylene, 25.1% glacial acetic acid and 2.5% oxygen was passed through the heated catalyst at a pressure of 110 psig and a contact time of three seconds. The reactor effluent was passed through three traps connected in series; one cooled with ice water and two traps held at dry-ice temperature. The liquid condensates were combined and analyzed for esters and free acetic acid (by alkaline titration and gas chromatography). The vent gases were analyzed by gas chromatography for ethylene, oxygen and carbon oxides. The analyses showed that 1,2-diacetoxyethane (ethylene glycol diacetate) was produced at the rate of 116 g/l. cat/hr in 62.8% Selectivity based on reacted acetic acid with complete conversion of oxygen (limiting reactant). A small amount of gamma-butyrolactone (1 g/l. cat/hr) was detected in the liquid condensate.

EXAMPLE 3

Oxyacylation of ethylene with acetic acid and oxygen at 85 psig and 300° C.

Example 2 was repeated except that the reaction was carried out at 85 psig and 300° C. The production rate of 1,2-diacetoxyethane was 113 g/l. cat/hr at 44.9% selectivity based on reacted acetic acid, with complete conversion of oxygen.

EXAMPLE 4

Oxyacylation of ethylene with acetic acid and oxygen at 60 psig and 300° C.

Example 3 was repeated except that the reactor pressure was 60 psig and the contact time was increased to four seconds. The production rate of 1,2-diacetoxyethane was 24.7 g/l. cat/hr at 69.4% selectivity based on reacted acetic acid. The oxygen conversion was 66.5%.

Various changes and modifications can be made in the process of this invention without departing from the spirit and scope thereof. The various embodiments disclosed herein were for the purpose of further illustrating the invention but were not intended to limit it.

What is claimed is:

1. A process for preparing ethylene glycol esters which comprises reacting ethylene, oxygen and a C$_2$ to C$_8$ carboxylic acid in the vapor phase at a pressure above about 40 psig in the presence of a catalytically effective amount of a catalyst consisting essentially of an oxide of uranium and at least one oxide selected from the group consisting of arsenic, antimony and bismuth oxides.

2. The process of claim 1 wherein the carboxylic acid is acetic acid.

3. The process of claim 1 wherein the catalyst consists essentially of an oxide of uranium and an oxide of antimony.

4. The process of claim 3 wherein the catalyst is supported and the catalyst contains about 5%-30% antimony and 1% to 20% uranium.

5. The process of claim 1 wherein the pressure is about 60 to 200 psig.

6. The process of claim 5 wherein the temperature is between about 150° and 400° C.

7. The process of claim 6 wherein the carboxylic acid is acetic acid.

8. The process of claim 7 wherein the catalyst is supported and consists essentially of an oxide of uranium and an oxide of antimony.

9. The process of claim 8 wherein the catalyst contains about 5%-30% antimony and 1% to 20% uranium.

* * * * *